US00PP32228P2

(12) United States Plant Patent
Koppe

(10) Patent No.: US PP32,228 P2
(45) Date of Patent: Sep. 22, 2020

(54) ***BEGONIA* PLANT NAMED 'KRSWESA01'**

(50) Latin Name: ***Begonia* x *hiemalis***
Varietal Denomination: KRSWESA01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/602,492

(22) Filed: Oct. 17, 2019

(51) Int. Cl.
*A01H 5/02* (2018.01)
*A01H 6/18* (2018.01)

(52) U.S. Cl.
USPC ..... Plt./348
CPC ..... *A01H 6/18* (2018.05)

(58) Field of Classification Search
USPC ..... Plt./348
CPC ..... A01H 5/02
See application file for complete search history.

(56) References Cited

PUBLICATIONS

PLUTO UPOVROM Plant Variety Database Citation for 'KRSWESA01' as per QZ PBR 20183103; Feb. 16, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Begonia* plant named 'KRSWESA01' characterized by its compact, broadly upright and mounded plant habit; moderately vigorous growth habit; moderately freely branching habit; dark green to greyed green-colored leaves; freely flowering habit; semi-double to double-type male flowers and single-type female flowers that are light salmon red in color and held above and beyond the foliar plane; and good postproduction longevity.

2 Drawing Sheets

Figure 1:
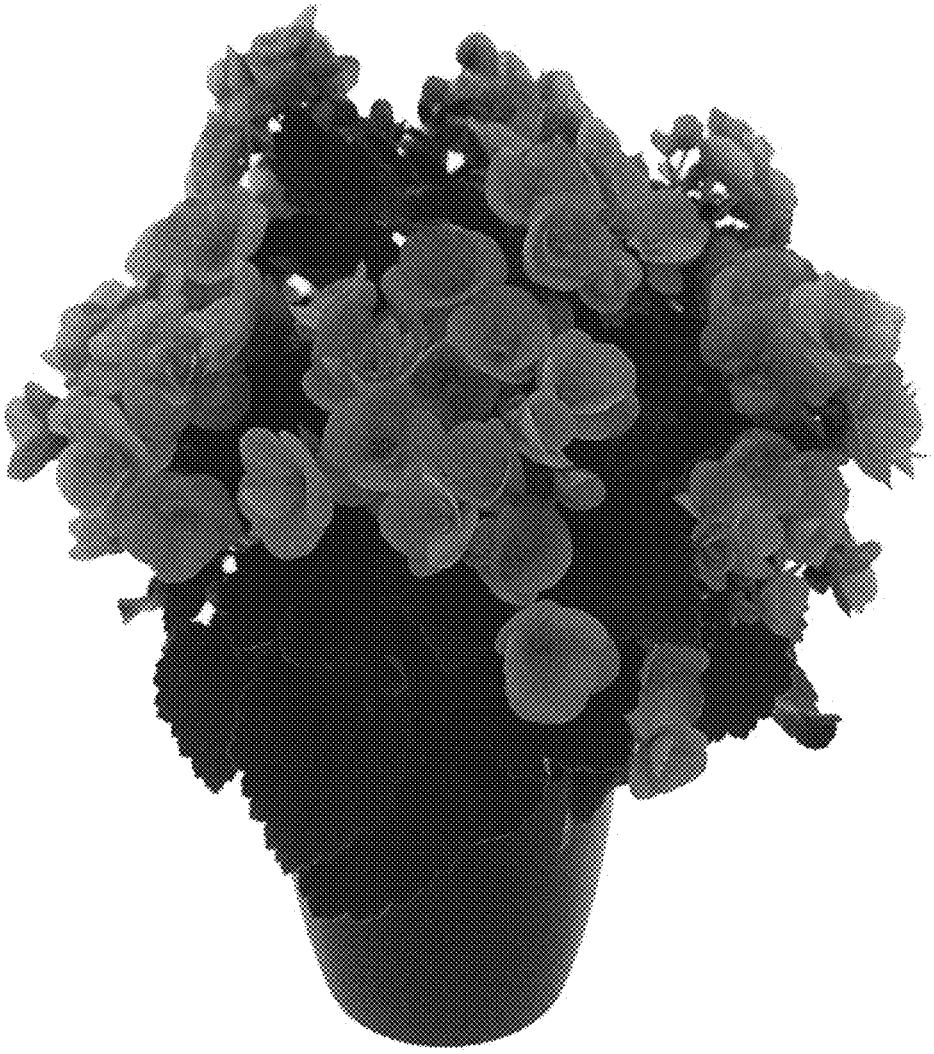

Botanical designation: *Begonia* x *hiemalis*
Cultivar denomination: 'KRSWESA01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRSWESA01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant originated from a cross-pollination made by the Inventor in Ermelo, The Netherlands in November, 2012 of a proprietary selection of *Begonia* x *tuberhybrida* identified as code number KV11K1897-008, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in December, 2013.

Asexual reproduction of the new *Begonia* plant by terminal vegetative cuttings taken in a controlled greenhouse environment in Ermelo, The Netherlands since February, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRSWESA01'. These characteristics in combination distinguish 'KRSWESA01' as a new and distinct *Begonia* plant:

1. Compact, broadly upright and mounded plant habit.
2. Moderately vigorous growth habit.
3. Moderately freely branching habit.
4. Dark green to greyed green-colored leaves.
5. Freely flowering habit.
6. Semi-double to double-type male flowers and single-type female flowers that are light salmon red in color and held above and beyond the foliar plane.
7. Good postproduction longevity.

Plants of the new *Begonia* differ primarily from plants of the female parent selection in the following characteristics:

1. Plants of the new *Begonia* are more compact than plants of the female parent selection.
2. Plants of the new *Begonia* have smaller flowers than plants of the female parent selection.
3. Plants of the new *Begonia* have light salmon red-colored flowers whereas plants of the female parent selection have apricot-colored flowers.

Plants of the new *Begonia* differ primarily from plants of the male parent selection in the following characteristics:

1. Plants of the new *Begonia* are more compact and uniform than plants of the male parent selection.

2. Plants of the new *Begonia* have semi-double to double-type male flowers whereas plants of the male parent selection have single-type male flowers.

Plants of the new *Begonia* can be compared to plants of *Begonia* x *hiemalis* 'Dark Netja', not patented. In side-by-side comparisons conducted in Ermelo, The Netherlands, plants of the new *Begonia* differ primarily from plants of 'Dark Netja' in the following characteristics:

1. Plants of the new *Begonia* are more compact than plants of 'Dark Netja'.
2. Plants of the new *Begonia* have darker-colored flowers than plants of 'Dark Netja'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'KRSWESA01' grown in a container.

Figure 2:
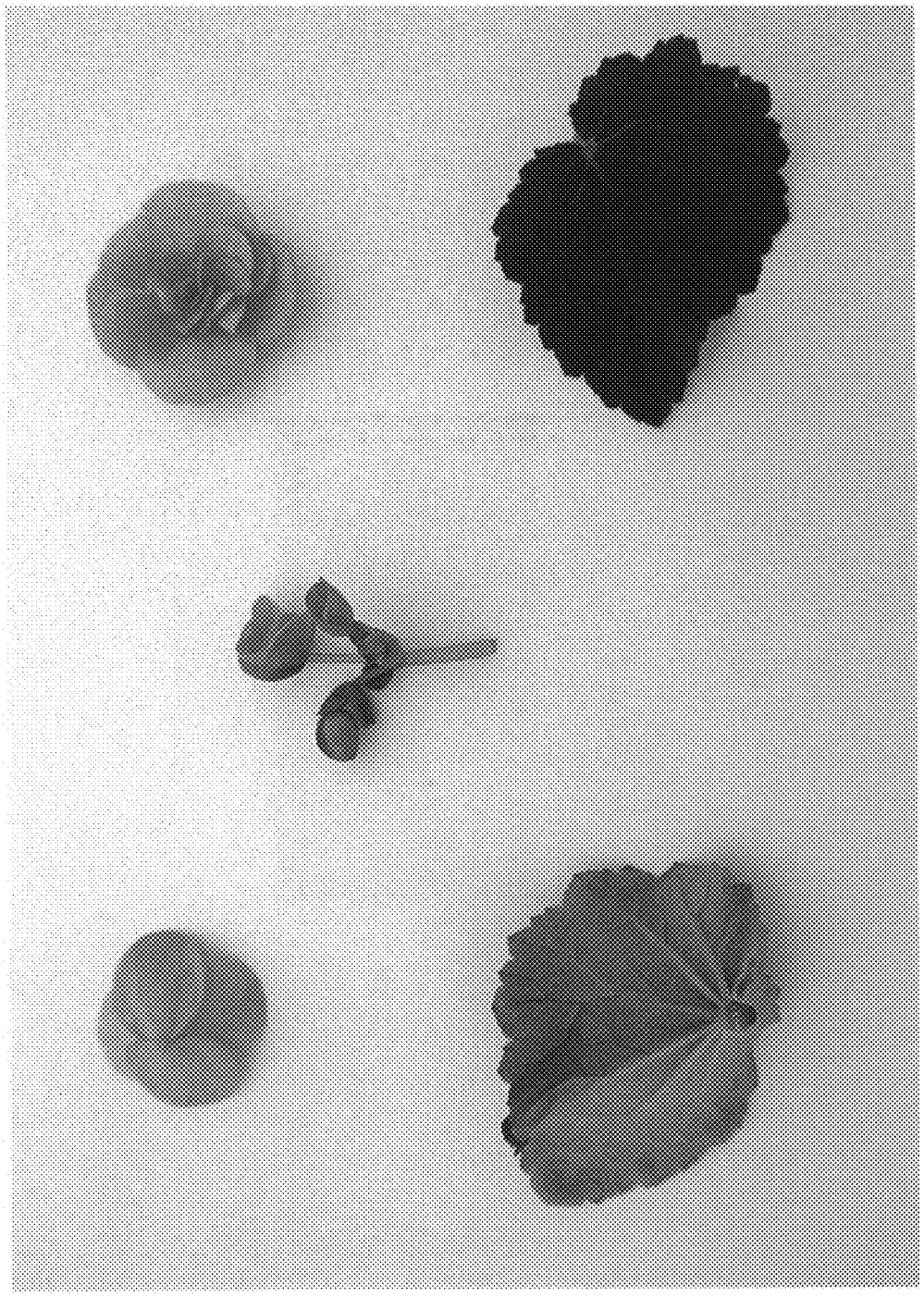

The photograph on the second sheet (FIG. 2 of 2) are close up views of the upper (right) and lower (left) surfaces of typical leaves and flowers of 'KRSWESA01', and in the center of the photograph is a close-up view of typical flower buds.

DETAILED BOTANICAL DESCRIPTION

The aforementioned photographs and following observations and measurements describe plants grown during the late spring and early summer in 10.5-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRSWESA01'.

Parentage:

*Female, or seed, parent*.—Proprietary selection of *Begonia* x *tuberhybrida* identified as code number KV11K1897-008, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Broadly upright and mounded plant habit; overall plant shape, globular.

*Growth habit*.—Moderately vigorous growth habit and moderate growth rate; suitable for 9-cm and larger containers; under optimal environmental and cultural conditions, usually about eleven weeks from rooted cuttings are required to produce proportional plants in 10.5-cm containers.

*Branching habit*.—Moderately freely branching with about five primary branches each with about three secondary branches developing per plant.

*Plant height, soil level to top of foliar plane*.—About 23.5 cm.

*Plant height, soil level to top of floral plane*.—About 25.2 cm.

*Plant width*.—About 33.3 cm.

*Lateral branches*.—Length: About 12 cm. Diameter: About 7 mm. Internode length: About 2.6 cm. Strength: Moderately strong. Aspect: Erect to about 60° from vertical. Texture and luster: Sparsely pubescent; slightly glossy. Color, developing: Close to 145B. Color, developed: Close to 152B. Lenticels: None observed on plants of the new *Begonia* to date.

*Leaves*.—Arrangement: Alternate, simple. Length: About 7.9 cm. Width: About 5.9 cm. Shape: Ovate to broadly ovate. Apex: Short apiculate. Base: Obliquely cordate, lobes free to slightly imbricate. Margin: Crenate to serrate; slightly undulate. Texture and luster, upper surface: Smooth, glabrous; velvety; slightly glossy. Texture and luster, lower surface: Smooth, glabrous; velvety; matte. Venation pattern: Laciniate, pinnate. Color: Developing leaves, upper surface: Close to between 141A and 143A. Developing leaves, lower surface: Close to 148B. Fully expanded leaves, upper surface: Slightly darker than between 139A and N189A; venation, close to 147B. Fully expanded leaves, lower surface: Close to 191A; venation, close to 146C to 146D. Petioles: Length: About 5.1 cm. Diameter: About 4 mm. Strength: Low, flexible. Texture and luster, upper and lower surfaces: Sparsely pubescent; slightly to moderately glossy. Color, upper surface: Close to 199B; distally, strongly tinged with close to 180A. Color, lower surface: Close to 199C; distally, slightly tinged with close to 180A. Stipules: Quantity and appearance: Two leafy stipules at the base of each leaf. Length: About 7 mm. Width: About 6 mm. Shape: Broadly ovate. Apex: Broadly acute. Base: Broadly cuneate. Margin: Ciliate. Color, upper and lower surfaces: Close to 145A to 145B.

Flower description:

*Flower form and flowering habit*.—Large semi-double to double- type male and single-type female rotate flowers arranged in axillary cymes; typically about five flowers per cyme, numerous cymes in flower simultaneously and about 300 flowers developing per plant; flowers face upright to outwardly and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height*.—About 10.7 cm.

*Inflorescence diameter*.—About 8.8 cm.

*Flower buds*.—Length: About 1.5 cm. Diameter: Ranging from about 1 cm to 1.7 cm. Shape: Broadly obovate to nearly circular, flattened. Texture and luster: Smooth, glabrous; velvety; matte. Color: Close to 39B.

*Female flowers*.—Diameter: About 4.5 cm. Depth: About 1.5 cm. Tepals: Quantity and arrangement: About seven arranged in three whorls. Length, inner and outer whorls: About 2 cm. Width, inner and outer whorls: About 2.1 cm. Shape: Broadly obovate to reniform. Apex: Obtuse to rounded. Base: Cuneate. Margin: Entire, not undulate. Texture and luster, upper surface: Smooth, glabrous; moderately velvety; matte. Texture and luster, lower surface: Smooth, glabrous; moderately velvety; slightly glossy. Color: When opening, upper surface: Close to 48C. When opening, lower surface: Close to 50C. Fully opened, upper surface: Close to 48B; at the base, slightly tinged with close to 153D; venation, similar to lamina color; color does not change with development. Fully opened, lower surface: Close to 48C; at the base, slightly tinged with close to 153D; venation, similar to lamina color; color does not change with development. Tepaloids: None observed on female flowers.

*Male flowers*.—Diameter: About 4.3 cm. Depth: About 1.4 cm. Tepals: Quantity and arrangement: About four arranged in two whorls. Length, inner whorl: About 2.1 cm. Length, outer whorl: About 2.2 cm. Width, inner whorl: About 2.1 cm. Width, outer whorl: About 2.4 cm. Shape, inner whorl: Broadly obovate to orbicular. Shape, outer whorl: Reniform to broadly ovate. Apex: Obtuse to rounded. Base: Cuneate. Margin: Entire, not undulate. Texture and luster, upper surface: Smooth, glabrous; moderately velvety; matte. Texture and luster, lower surface: Smooth, glabrous; moderately velvety; slightly glossy. Color: When opening, inner and outer whorls, upper surface: Close to 48C. When opening, inner whorl, lower surface: Close to 48C. When opening, outer whorl, lower surface: Close to 48A to 48B. Fully opened, inner and outer whorls, upper surface: Close to 48C; at the base, slightly tinged with close to 153D; venation, similar to lamina color; color does not change with development. Fully opened, inner whorl, lower surface: Close to 48C; at the base, slightly tinged with close to 153D; venation, similar to lamina color; color does not change with development. Fully opened, outer whorl, lower surface: Close to 47C and 48A; venation, similar to lamina color; color does not change with development. Tepaloids: Quantity and arrangement per flower: Typically about 20 per flower arranged in about four whorls. Length: About 0.4 cm to 2.1 cm. Width: About 0.2 cm to 2 cm. Shape: Obovate. Apex: Obtuse to rounded. Base: Cuneate to broadly cuneate. Margin: Entire; not undulate. Texture and luster, upper and lower surfaces: Smooth, glabrous; moderately velvety; matte. Color: When opening, upper and lower surfaces: Close to 48C. Fully opened, upper and lower surfaces: Close to 48C; towards the base, slightly tinged with close to 153D; venation, similar to lamina color; color does not change with development.

*Flower bracts*.—Quantity and arrangement: Two positioned at the top of the peduncle. Length: About 1 cm. Width: About 1.1 cm. Shape: Broadly ovate to reniform. Apex: Obtuse to broadly and bluntly acute. Base: Broadly cuneate. Margin: Finely ciliate. Texture and luster, upper and lower surfaces: Smooth, glabrous; slightly glossy. Color, upper and lower surfaces: Close to 147C; towards the margins and apex, tinged with close to 178C.

*Peduncles*.—Length: About 5 cm. Diameter: About 4 mm. Strength: Moderately strong. Aspect: About 35° from lateral branch axis. Texture and luster: Sparsely pubescent; moderately glossy. Color: Close to between 152A and N199B; proximally, close to 146B.

*Pedicels*.—Length: About 2.6 cm. Diameter: About 2 mm. Strength: Moderately strong. Aspect: About 22.5° from peduncle axis. Texture and luster: Moderately pubescent; moderately glossy. Color, upper surface: Close to 174B; distally, close to 179A. Color, lower surface: Close to 174B.

*Reproductive organs*.—Stamens (present on male flowers only): No stamens observed as all stamens transformed into tepaloids. Pistils (present on female flowers only): Quantity per flower: About six, fused in pairs. Pistil length: About 7 mm. Style length: About 6 mm. Style color: Close to N34B. Stigma color: Close to 22A. Ovary color: Close to 146C; apex, close to 173B.

*Seeds and fruits*.—To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KRSWESA01' as illustrated and described.

* * * * *